(12) United States Patent
Boland et al.

(10) Patent No.: US 8,430,590 B2
(45) Date of Patent: Apr. 30, 2013

(54) ELECTRIC TOOTHBRUSH

(75) Inventors: Bernhard Boland, Frankfurt am Main (DE); Uwe Bielfeldt, Bad Soden (DE); Christof Miltenberger, Neu-Anspach (DE); Peter Schaefer, Waldbrunn (DE); Norbert Schaefer, Frankfurt am Main (DE); Michael Sauer, Bad Camberg (DE)

(73) Assignee: Braun GmbH, Kronberg (DE)

( * ) Notice: Subject to any disclaimer, the term of this patent is extended or adjusted under 35 U.S.C. 154(b) by 512 days.

(21) Appl. No.: 12/600,734

(22) PCT Filed: May 26, 2008

(86) PCT No.: PCT/EP2008/004162
§ 371 (c)(1),
(2), (4) Date: Jun. 14, 2010

(87) PCT Pub. No.: WO2008/145320
PCT Pub. Date: Dec. 4, 2008

(65) Prior Publication Data
US 2010/0278582 A1    Nov. 4, 2010

(30) Foreign Application Priority Data
May 30, 2007  (DE) .......................... 10 2007 025 386

(51) Int. Cl.
*B43K 5/02*      (2006.01)
*A46B 11/04*     (2006.01)
(52) U.S. Cl.
USPC ...................................... 401/188 R; 401/282

(58) Field of Classification Search .............. 401/188 R, 401/282, 283, 284, 269; 15/22.2, 110, 167.1–167.3; 433/80, 82, 89
See application file for complete search history.

(56) References Cited

U.S. PATENT DOCUMENTS

| | | | | |
|---|---|---|---|---|
| 4,060,870 A * | 12/1977 | Cannarella | ........................ | 15/24 |
| 4,315,741 A * | 2/1982 | Reichl | ............................. | 433/82 |
| 6,648,641 B1 * | 11/2003 | Viltro et al. | ..................... | 433/80 |
| 6,902,337 B1 * | 6/2005 | Kuo | .......................... | 401/188 R |
| 6,918,153 B2 * | 7/2005 | Gruber | .......................... | 15/22.1 |
| 7,896,567 B2 * | 3/2011 | Burrowes | ...................... | 401/190 |
| 7,993,067 B2 * | 8/2011 | Hall et al. | ................. | 401/188 R |
| 2007/0251034 A1 * | 11/2007 | Meressa et al. | .................... | 15/23 |

FOREIGN PATENT DOCUMENTS

DE           19935067 A1 *  2/2001

* cited by examiner

*Primary Examiner* — David Walczak
*Assistant Examiner* — Jennifer C Chiang
(74) *Attorney, Agent, or Firm* — John P. Colbert; Vladimir Vittenberg

(57) ABSTRACT

An electric toothbrush is disclosed. The toothbrush includes a handle part and an attachment part, wherein the handle part has a housing, in which a reservoir for a care substance, a pump for delivering the care substance and a drive unit for driving the pump are arranged. The housing is divided into a liquid-tight first chamber and a second chamber by a partition extending in the longitudinal direction of the housing. The first chamber housing the drive unit is arranged in the first chamber and the reservoir and the pump are arranged in the second chamber.

16 Claims, 5 Drawing Sheets

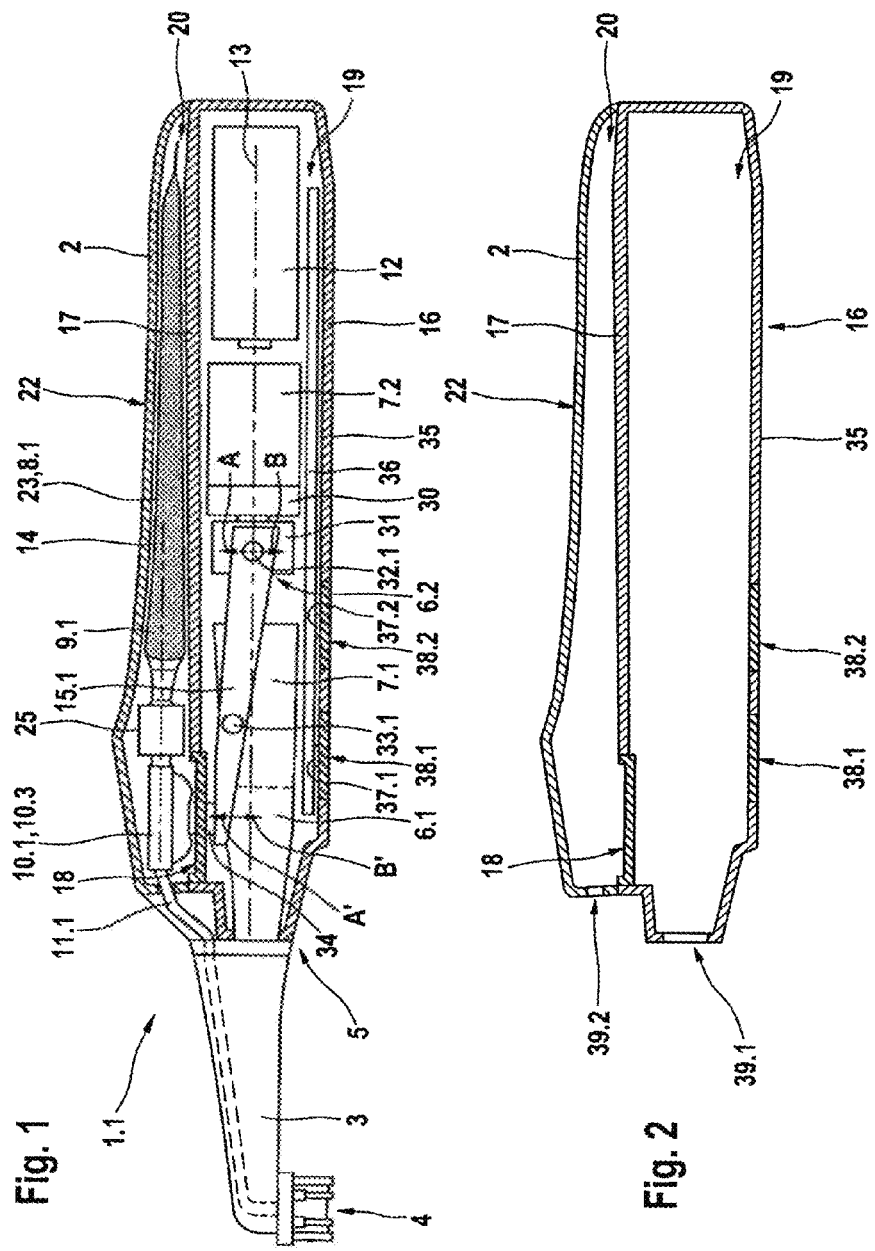

ELECTRIC TOOTHBRUSH

The invention relates to an electric toothbrush comprising a handle part and an attachment part, wherein the handle part has a housing in which a reservoir for a care substance, a pump for delivering the care substance and a drive unit for driving the pump are arranged.

From U.S. Pat. No. 6,957,925-B1, an electric toothbrush is known that has a handle part and an attachment comprising a brush head that is driven by a first electric motor arranged in the handle part. A reservoir is arranged inside the handle part for a liquid dental care product (toothpaste) that is connected via a pump to a canal that discharges into the bristle head. The pump is driven continuously or in specified intervals by a second electric motor, wherein the first and second electric motor is powered by a disposable or a rechargeable battery. This eliminates the need to manually apply a dental care product from a separate tube onto the bristle head and results in a more even distribution of the dental care product on the teeth, thereby achieving an improved care result. This electric toothbrush has disadvantage, for example, that a possible leaking of a dental care product from the reservoir can result in a malfunction of the electrical or electronic system caused by corresponding leakage currents and/or corrosions.

On the other hand, the object of the invention is to create an electric toothbrush that ensures a high degree of operational reliability and in addition has a compact design and is therefore comfortable to handle.

This object is achieved by an electric toothbrush having a handle part and an attachment part, wherein the handle part has a housing that is divided into a liquid-tight first chamber and a second chamber by a partition that extends in the longitudinal direction of the housing, wherein a reservoir for a care substance and a pump are arranged in the second chamber and a drive unit for the pump is arranged in the first chamber. The second chamber of the housing is accessible from the outside by means of a recloseable cover part.

The reservoir contains a liquid or pasty agent for treating the oral cavity. These may be for example substances for tooth cleaning and agents for cavity prevention, gum treatment, halitosis reduction, tooth bleaching or lightening, remineralization of dentin, or desensitizing sensitive teeth. If the electric toothbrush has two reservoirs, the reservoirs can contain two different substances that can be delivered in parallel by two pumps. This is especially advantageous if multiple substances are to be used for oral care that cannot be stored together because they would otherwise react with each other. Because of the separate storage in two reservoirs and parallel delivery by means of two pumps, these substances only mix once they are in the mouth and can thus be administered simultaneously. In addition, positive effects may result when two substances react with each other in the mouth.

The reservoir preferably consists of a replaceable bag made of a flexible foil that has, for example, a multi-layer structure composed of metal- and plastic foils and preferably has an elongated, low-profile shape. When removing the oral care product during pumping the reservoir collapses as a result of the created negative pressure. The pump can optionally be controlled by the user via an operating push-button or by means of an electronic circuit. The electric toothbrush can also contain a plurality of reservoirs that are preferably arranged side by side and may be combined into a replaceable unit.

The reservoir has a connecting piece for connection coupling to the pump; said connecting piece is equipped with a single-actuation valve or a valve that can be actuated multiple times. The pump is connected to a coupling part for connection of the reservoir; said coupling part has an inlet valve that is preferably arranged within a connecting nozzle and that is forced to open by means of a tappet fixed on the reservoir when the reservoir is being connected. The valves prevent the pump and/or reservoir from drying out. Furthermore, detent elements are preferably attached on the connecting piece of the reservoir that can lock with the coupling part of the pump.

The pump, in combination with the coupling part and an outlet that is connected via a canal, forms a replaceable assembly. The replaceable assembly can also comprise a plurality of pumps with a plurality of inlets in the coupling piece and a plurality of outlets connected via canals. The outlets can be connected to canals in the attachment part.

The attachment part consists, for example, of a bristle head that is known per se, which can be replaceably connected to the handle part. The bristle head can be provided with a movable bristle field that is drivable by means of a first drive unit in the handle part. The first drive unit is likewise arranged in the liquid-tight first chamber. The bristle head additionally has an outlet opening for the care substance that is connectable via a canal to the pump and to the reservoir. Preferably, a second drive unit for the pump is present in the handle part, so that dosing the care substance is independent of the drive for the bristle field. This allows, for example, a larger quantity of the care substance to be delivered at a higher rate of delivery at the beginning of the tooth brushing process, in order to then continuously re-supply at a lesser rate of delivery only an amount of care substance needed for the remaining brushing time. In order to achieve a compact design of the toothbrush, the drive unit for the attachment part and the drive unit for the pump are preferably arranged one behind the other in the longitudinal direction of the housing in the first chamber.

The partition between the two chambers can be partially designed as soft-elastic, wherein the transmission of a driving movement from the drive unit to the pump results in the soft-elastic region of the partition. In the case of a rigid partition, a liquid-tight slide passage, for example, is provided that enables the driving movement to be transmitted from the drive unit to the pump. In both cases, the transmission of the driving movement can take place via a lever that can optionally also actuate a plurality of pumps.

The soft-elastic portion of the partition consists of a flexible membrane comprising elements of a hard plastic material, around which the soft-elastic plastic of the membrane is injection molded. These elements are designed in the form of transmitting pins or they are designed so as to accommodate cylindrical transmitting pins. The transmitting elements are actuated at one end by the lever and are connected on their other side in a form-fitting or non-positive manner to the pump, preferably directly to the elastic diaphragm of a diaphragm valve pump. The actuation of the pump can take place in a positive manner, i.e. the lever both presses and also pulls on the pump diaphragm, such that the pump does not require a reset spring. If the pump does have a reset spring, however, the lever needs to only exert pressure on the pump diaphragm via the transmitting elements, since resetting of the pump diaphragm takes place by means of the reset spring.

The invention will be explained in more detail with the aid of three exemplary embodiments shown in the Figures, in which:

FIG. 1 shows, in a cross-sectional side view, an electric toothbrush with a bristle attachment part, a reservoir, and a housing partition having an integrated soft membrane for transmitting pumping movements, as a first exemplary embodiment;

FIG. 2 shows, in a cross-sectional side view, a housing of the electric toothbrush according to FIG. 1;

Figure 3:
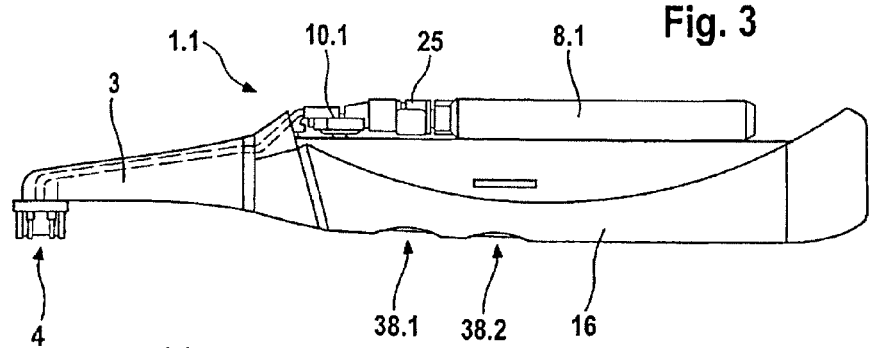
FIG. 3 shows, in a side view, the electric toothbrush according to FIG. 1, but without a back cover part.

FIG. 1 shows a first exemplary embodiment, in a cross-sectional side view, of an electric toothbrush 1.1 having a bristle attachment part 3 and a reservoir 8.1. The first electric toothbrush 1.1 has a handle part 2 and a (replaceable) attachment part 3 having a bristle head 4, wherein the attachment part 3 is attachable to a front end 5 of the handle part 2, and the bristle head 4 is drivable by a first drive unit 6.1 comprising a first electric motor 7.1.

The handle part 2 has a reservoir 8.1 for a liquid dental care product 9.1. The reservoir 8.1 is connected via a pump 10.1 to a canal 11.1 that discharges into the bristle head 4. The pump 10.1 is drivable by a second drive unit 6.2 having a second electric motor 7.2, wherein the first and the second electric motor 7.1, 7.2 is powered by a disposable or a rechargeable battery 12.

Because a housing 16 of the handle part 2 forms, by means of a liquid-tight, elongated partition 17, a first and a second chamber 19, 20 that are arranged side by side, a high degree of operational reliability is achieved, since the electrical components (drive units with motors, rechargeable battery, control unit, etc.) are separated from the delivery system (pump 10.1, canal 11.1, or the reservoir 8.1). A malfunction of the electrical or electronic system caused by corresponding leakage currents and/or corrosions resulting from dental care product 9.1 leaking from a reservoir 8.1 or other liquid entering from outside—such as rinsing water—is thus reliably prevented.

The first and the second drive unit 6.1, 6.2, and the disposable or rechargeable battery 12 are arranged one behind the other in a first row 13 in the first chamber 19, and the first reservoir 8.1 and the first pump 10.1 are arranged one behind the other in a second row 14 in the second chamber 20, wherein the first and second row 13, 14 of components are arranged side by side in the first and the second chamber 19, 20, this results in a compact, convenient handle part 2, and a compact and slim design and comfortable handling of the electric toothbrush 1.1.

The first drive unit 6.1 and the pump 10.1 are arranged at the front end 5 of the handle part 2. The pump 10.1 is drivable by means of the second drive unit 6.2 via a lever 15.1, wherein the second drive unit 6.2 transmits back and forth movements A-B to the lever 15.1 by means of a drive pin 32, which are transmitted as pumping movements A'-B' from the other end of the lever 15.1 via an integrated, rubber-elastic soft membrane 18 of the partition 17 by means of non-positive, rubber-elastic contact to the pump 10.1, or diaphragm valve pump 10.3. The lever 15.1 is arranged on one side next to the first drive unit 6.1, wherein the lever 15.1 corresponds with the diaphragm valve pump 10.3.

The integrated soft membrane 18 maintains the liquid-tight separation between the first and second chamber 19, 20 by the partition 17. The integrated soft membrane 18 preferably has a (circular) round surface area and forms part of the partition 17.

Because the rubber-elastic diaphragm of the diaphragm valve pump 10.3 has a reset force, complete pumping movements of the diaphragm valve pump 10.3 are attained.

The second chamber 20 has on its outside a recloseable cover part 22, thereby permitting an easy replacement of a reservoir 8.1 or convenient refilling of a dental care product 9.1. The reservoir 8.1 is preferably designed with a low-profile shape and preferably consists essentially of a plastic foil 23.

Figure 10:
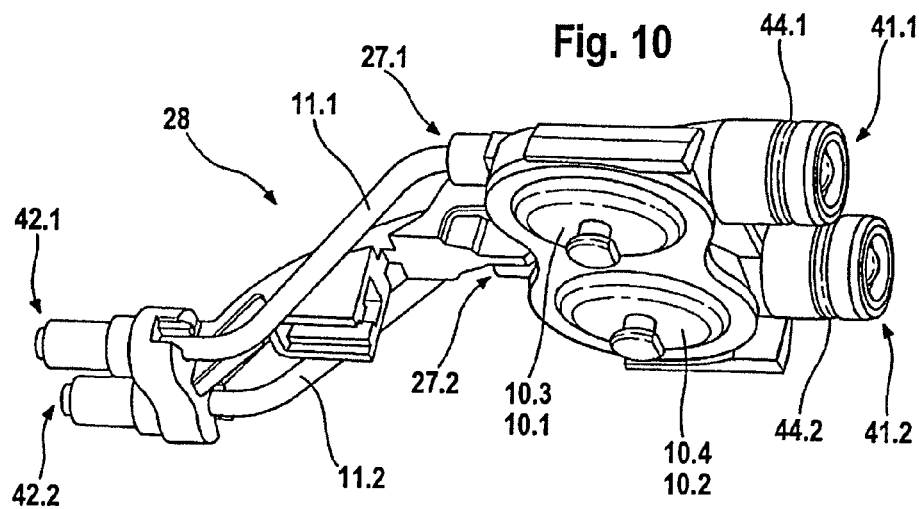
FIG. 10 shows, in a perspective view, a first and second pump with two inlets and two outlets as one assembly.

In order to connect the reservoir 8.1 to the diaphragm valve pump 10.3, a coupling part 25 is provided (additional details will become apparent from FIG. 11) that has a fixing means 25.1 for manual replacement of the reservoir 8.1, said fixing means 25.1 fixing a neck 40.1 (FIG. 11) of the reservoir 8.1. The diaphragm valve pump 10.3 is connected on the outlet side via a canal 11.1 to an outlet 42.1 (FIG. 10).

The second drive unit 6.2 is formed by a second electric motor 7.2 having a gear box 30 (with a reduction ratio of, for example, 1:60), that carries out corresponding back and forth movements A-B by means of a drive pin 32, which are transmitted to the lever 15.1. In this process, the back and forth movements A'-B' of the lever 15.1 are transmitted via a stationary rotary joint 33 by means of a tappet 34 via contact through the soft membrane 18 of the partition 17 to the first pump 10.1.

An electronic circuit board 36 having a control unit and a first and second switch 37.1, 37.2 (e.g. on/off switch 37.1 and program switch 37.2 for delivering the dental care product 9.1) is arranged between the first row 13 of components (first and second drive unit 6.1, 6.2, and rechargeable battery 12) and a front housing wall 35, which can be actuated manually via a first or second soft-elastic housing wall zone 38.1, 38.2 for controlling the first electric toothbrush 1.1.

FIG. 2 shows, in a cross-sectional side view, only the housing 16 of the first electric toothbrush 1.1 with the partition 17 according to FIG. 1. The front end of the housing 16 has a first opening 39.1, through which the first drive unit 6.1 can drive the bristle head, and a second opening 39.2 as a passage for the canal 11.1

FIG. 3 shows, in a side view, the first electric toothbrush 1.1 according to FIG. 1, but without a cover part 22. In this state the reservoir 8.1 can be replaced.

Figure 4:
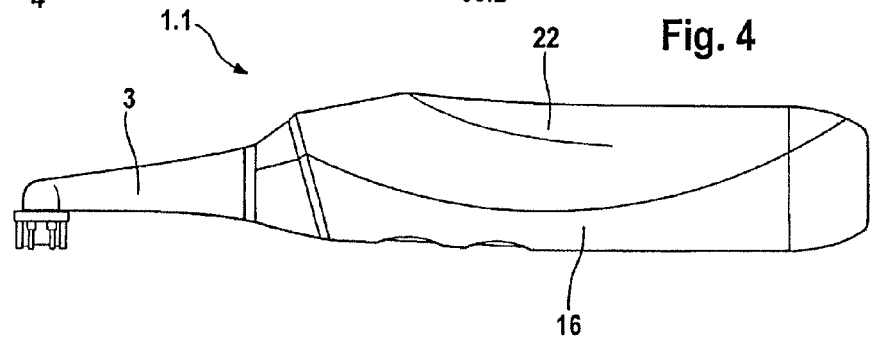
FIG. 4 shows, in a side view, the electric toothbrush according to FIG. 3, but with a back cover part.

FIG. 4 shows, in a side view, the first electric toothbrush 1.1 according to FIG. 3, but with a recloseable cover part 22 that closes the second chamber 20.

Figure 5:
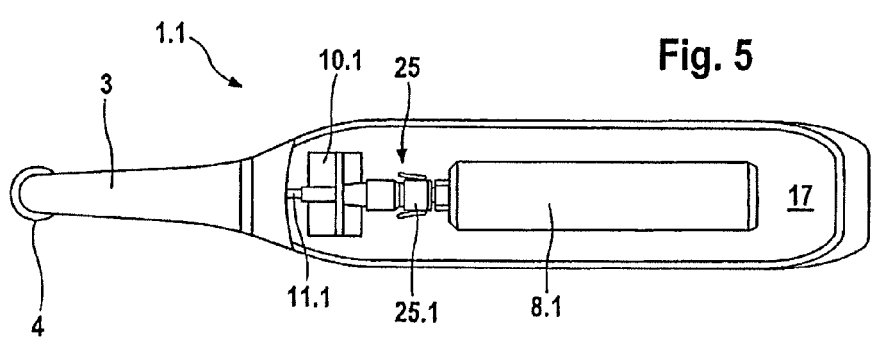
FIG. 5 shows, in a schematic rear view, the electric toothbrush according to FIG. 3 with a reservoir.

FIG. 5 schematically shows the first electric toothbrush 1.1 according to FIG. 3 with the first reservoir 8.1 in a rear view, from which the position of the reservoir 8.1 with the coupling part 25 and a fixing device 25.1 is apparent in more detail.

Figure 6:
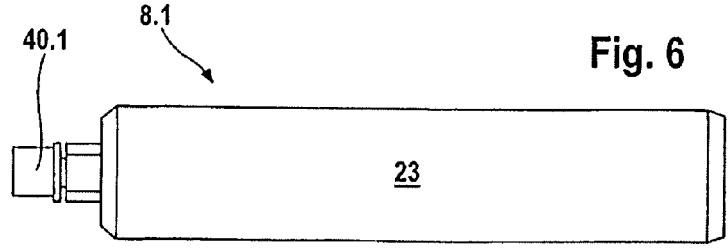
FIG. 6 shows, in an enlarged detail view, the reservoir according to FIG. 5.

FIG. 6 shows, in an enlarged detail view, the reservoir 8.1 according to FIG. 5, wherein a neck 40.1 for connecting to the coupling part 25 is shown.

Figure 7:
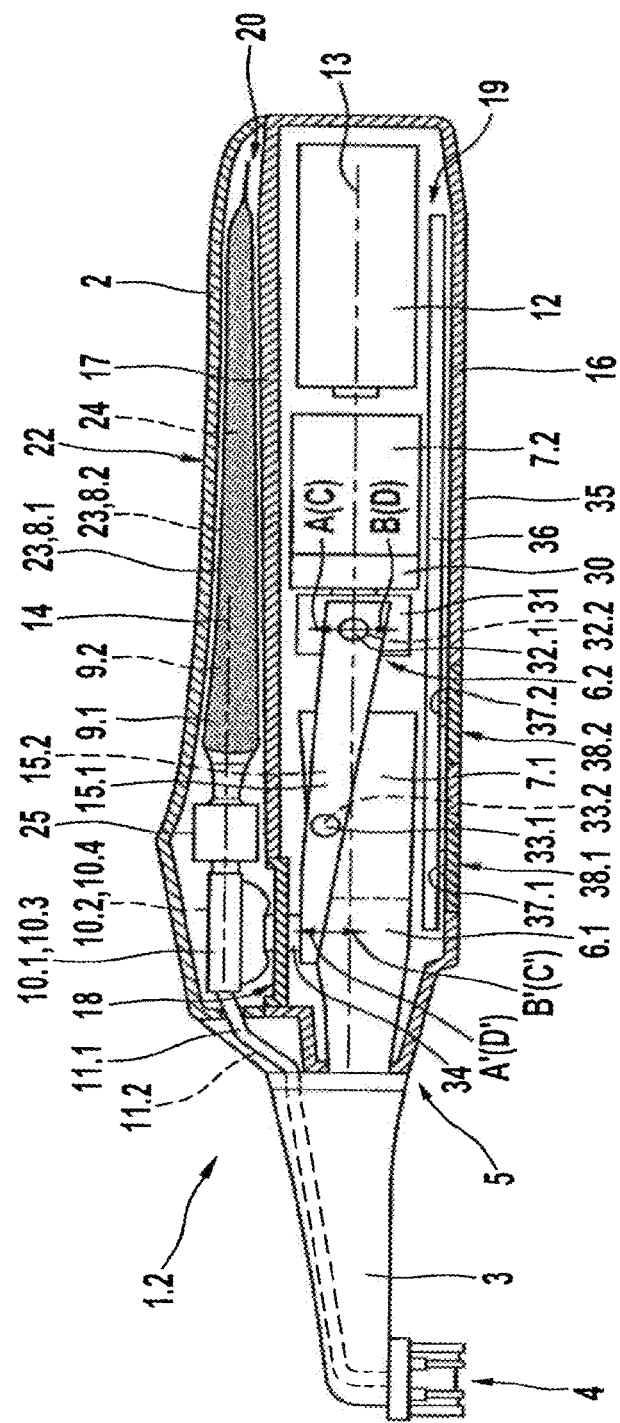
FIG. 7 shows, in a cross-sectional side view, an electric toothbrush with a bristle attachment part, two reservoirs arranged side by side, and a housing partition having an integrated soft membrane for transmitting pumping movements, as a second exemplary embodiment.

FIG. 7 shows, as a second exemplary embodiment, a second electric toothbrush 1.2 that corresponds to the first exemplary embodiment according to FIG. 1, but has a first and a second reservoir 8.1, 8.2, a first and a second diaphragm valve pump 10.3, 10.4, a first and a second canal 11.1, 11.2 to the bristle head 4, and a device 31 having a first and a second lever 15.1, 15.2.

The second electric toothbrush 1.2 has a handle part 2 featuring a (replaceable) attachment part 3 having a bristle head 4, wherein the attachment part 3 is fixable to a front end 5 of the handle part 2, and the bristle head 4 is drivable by a first drive unit 6.1 comprising a first electric motor 7.1.

The handle part 2 has a first and a second reservoir 8.1, 8.2 for a first and a second liquid dental care product 9.1, 9.2. The respective first and second reservoir 8.1, 8.2 are connected via a respective first and second pump 10.1, 10.2 to a respective first and second canal 11.1, 11.2, which discharge into the bristle head 4. The first and second pump 10.1, 10.2 are drivable by a second drive unit 6.2 comprising a second electric motor 7.2, wherein the first and the second electric motor 7.1, 7.2 are powered by a disposable or a rechargeable battery 12.

Because a housing 16 of the handle part 2 forms, by means of a liquid-tight, elongated partition 17, a first and a second chamber 19, 20 that are arranged side by side, a high degree of operational reliability is achieved, since the electrical components (drive units with motors, rechargeable battery, control unit, etc.) are separated from the delivery system (pumps 10.1, 10.2, canals 11.1, 11.2, or the reservoirs 8.1, 8.2). A malfunction of the electrical or electronic system caused by corresponding leakage currents and/or corrosions resulting from a dental care product leaking from a reservoir 8.1, 8.2, or other liquid entering from outside—such as rinsing water—is thus reliably prevented.

The first and the second drive unit 6.1, 6.2, and the disposable or rechargeable battery 12 are arranged one behind the other in a first row 13 in the first chamber 19, and the first and the second reservoir 8.1, 8.2 and the first and the second pump 10.1, 10.2 are arranged one behind the other in a second row 14 in the second chamber 20, wherein the first and second row 13, 14 of components are arranged side by side in the first and the second chamber 19, 20, this results in a compact, convenient handle part 2, and a compact and slim design and comfortable handling of the electric toothbrush 1.2.

The first drive unit 6.1 and the first and second pump 10.1, 10.2 are arranged at the front end 5 of the handle part 2.

The first and second pump 10.1, 10.2 are drivable by means of the second drive unit 6.2 via a respective first and second lever 15.1, 15.2, wherein the second drive unit 6.2 transmits back and forth movements A-B, C-D by means of a respective first and second drive pin 32.1, 32.2 to the respective first and second lever 15.1, 15.2, said back and forth movements A-B, C-D is transmitted as pumping movements A'-B', C'-D' from the other end of the respective first and second lever 15.1, 15.2 via non-positive, rubber-elastic contact through an integrated, rubber-elastic soft membrane 18 of the partition 17 to the respective first and second pump 10.1, 10.2, or first and second diaphragm valve pump 10.3, 10.4, respectively. The integrated soft membrane 18 maintains the liquid-tight separation between the first and second chamber 19, 20 by the partition 17. The integrated soft membrane 18 preferably has a (circular) round surface area and forms part of the partition 17.

Because the rubber-elastic diaphragms of the diaphragm valve pumps 10.3, 10.4 have a reset force, complete pumping movements of the diaphragm valve pumps 10.3, 10.4 are attained.

The first and the second lever 15.1, 15.2 are arranged on both sides of the first drive unit 6.1, wherein the first lever 15.1 corresponds with the first diaphragm valve pump 10.3 and the second lever 15.2 corresponds with the second diaphragm valve pump 10.4.

The second chamber 20 has on its outside a recloseable cover part 22, thereby permitting an easy replacement of one or more reservoirs 8.1, 8.2 or convenient refilling of a dental care product 9.1, 9.2. The reservoirs 8.1, 8.2 are preferably designed with low-profile shapes and preferably consist essentially of a plastic foil 23.

In order to connect the respective first and second reservoir 8.1, 8.2 to the respective first and second diaphragm valve pump 10.3, 10.4, a coupling part 25 is provided (additional details will become apparent from FIG. 11) that has a fixing means 25.1 for manual replacement of the respective first and second reservoir 8.1, 8.2; said fixing means 25.1 fixes a first neck 40.1 (FIG. 11) of the first reservoir 8.1 and a second neck 40.2 (FIG. 11) of the second reservoir 8.2. The first diaphragm valve pump 10.3 is connected on the outlet side via a first canal 11.1 to a first outlet 42.1 (FIG. 10) and the second diaphragm valve pump 10.4 is connected on the outlet side via a second canal 11.2 to a second outlet 42.2.

The second drive unit 6.2 is formed by the second electric motor 7.2 having a gear box 30 (with a reduction ratio of, for example, 1:60), that is connected to a device 31 that from the rotational revolutions of the gear box 30 carries out corresponding back and forth movements A-B by means of a first and a second drive pin 32.1, 32.2, which are transmitted to the respective first and second lever 15.1, 15.2. The back and forth movements A'-B' of the respective first and second lever 15.1, 15.2 are transmitted by means of a respective first and second stationary rotary joint 33.1, 33.2 via contact via the soft membrane 18 of the partition 17 to the respective first and second pump 10.1, 10.2.

An electronic circuit board 36 having a control unit and a first and second switch 37.1, 37.2 is arranged between the first row 13 of components (first and second drive unit 6.1, 6.2 and rechargeable battery 12) and a front housing wall 35 is, which can be actuated manually via a respective first and a second soft-elastic housing wall zone 38.1, 38.2 for controlling the second electric toothbrush 1.2.

In order to dispense the second liquid dental care product 9.2, a second pump 10.2 is provided that is optionally drivable by a third drive unit (not shown) arranged in a row, or by means of the device 31 (FIG. 7) of the second electric motor 7.2. With the third drive unit, an additional electric motor and a longer lever would be required. The first and/or the second dental care product 9.1, 9.2 can thus be delivered one after the other or in parallel and additionally also with specified volume flow profiles.

Figure 8:
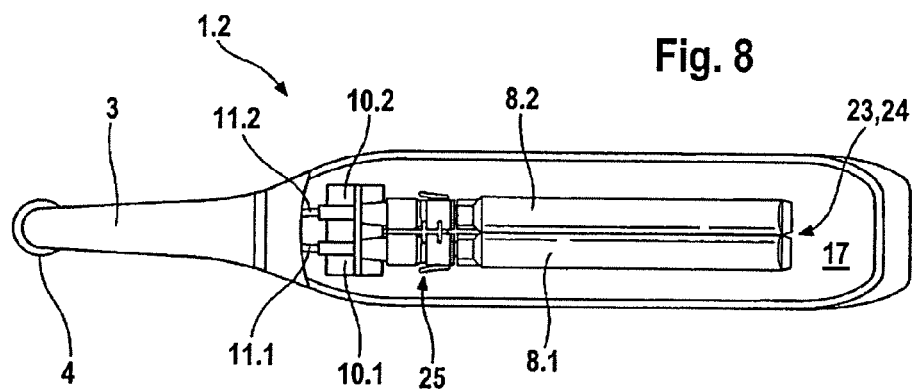
FIG. 8 shows, in a rear view, the electric toothbrush according to FIG. 7, with two reservoirs arranged side by side.

FIG. 8 shows the second electric toothbrush 1.2 in a rear view analogous to FIG. 5, but with a first and a second reservoir 8.1, 8.2 that are arranged side by side and can easily be replaced manually by means of a corresponding clamping device. In this manner an additional application of the second electric toothbrush 1.2 is thus optionally made possible by simple measures in that a second liquid dental care product 9.2 is used from a second reservoir 8.2. This second liquid dental care product 9.2 can preferably be made in such a way that it supplements the first dental care product 9.1 in the tooth care.

Figure 9:
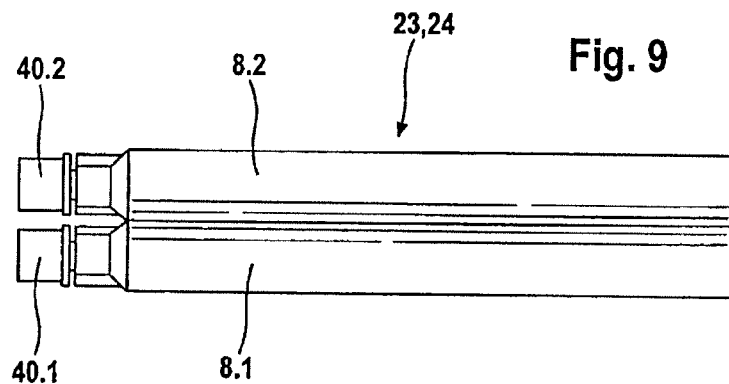
FIG. 9 shows, in an enlarged detail view, the two side-by-side reservoirs according to FIG. 8.

FIG. 9 shows, in an enlarged detail view, the side-by-side reservoirs 8.1, 8.2 according to FIG. 8, that have a respective first and second neck 40.1, 30.2 for connecting to the coupling part 25 and for discharging the dental care products 9.1, 9.2.

For better illustration, FIG. 10 shows, in a perspective view, the first and second pump 10.1, 10.2 with the first and second inlet 41.1, 41.2, which are connected via a respective first and second outlet opening 27.1, 27.2 to the respective first and second canal 11.1, 11.2, which have at their ends a respective first and second outlet 42.1, 42.2 and as a whole form an assembly 28. The assembly 28 provides for a simple assembly and optionally simple interchangeability.

Figure 11:
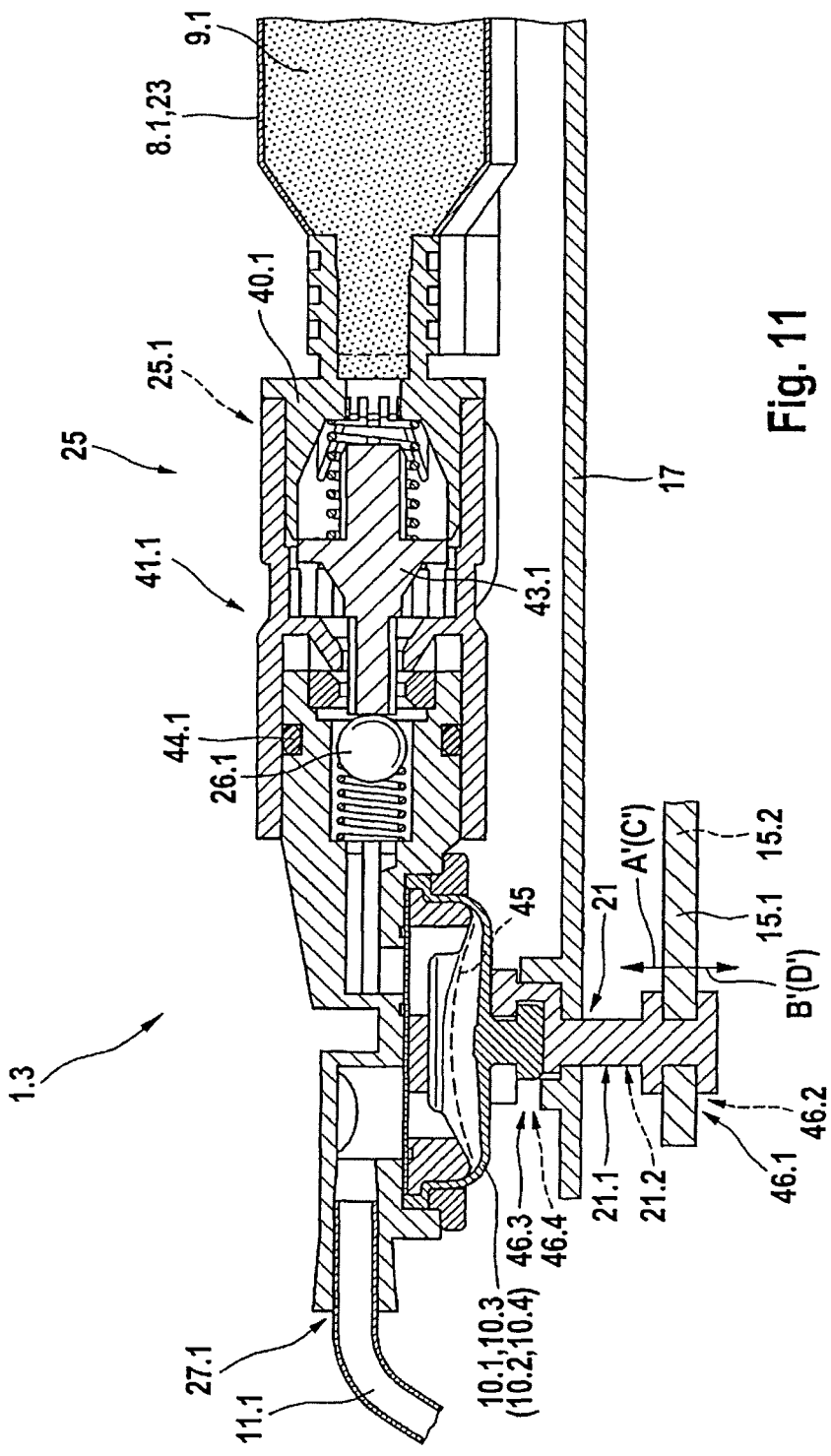
FIG. 11 shows, in a cross-sectional view, a portion of a toothbrush with a liquid-tight slide passage through the housing partition for transmitting pumping movements, and a connection of a reservoir, as a third exemplary embodiment.

FIG. 11 shows in a third exemplary embodiment a third electric toothbrush 1.3 having a liquid-tight slide passage 21 through the partition 17 for transmitting pumping movements A'-B', C'-D', and a connection of the first reservoir 8.1 with the coupling part 25, which is connected to the first inlet 41.1 of the first diaphragm valve pump 10.3. The coupling part 25 has a first inlet valve 26.1 that is actuated by connecting the first reservoir 8.1 through the first neck 41.1 by means of a first valve tappet 43.1. The inlet valve 26.1 prevents the first dental care product 9.1 from plugging up/drying out when the reservoir 8.1 is removed. A first sealing ring 44.1 ensures a mechanical and liquid-tight connection of the coupling part 25. In the embodiment for a twin container 24 all elements are arranged in duplicate and preferably form one unit.

The transmission of the respective pumping movements A'-B' and C'-D' to the respective first and second pump 10.1, 10.2 takes place via the respective first and second lever 15.1, 15.2 by means of non-positive contact via a respective first and second slide 21.1, 21.2 via a respective liquid-tight slide passage 21 in each case through the partition 17. On the one hand, the respective first and second slide 21.1, 21.2 is connected in a vibration-tight manner both via a respective first connection 46.1 and second connection 46.2 to the respective first and second lever 15.1, 15.2, and on the other hand via a respective third and fourth connection 46.3, 46.4 to the diaphragm of the respective first and second diaphragm valve pump 10.3, 10.4. The actuated state of the respective first and second diaphragm valve pump 10.3, 10.4 is shown by a dotted line 45.

The above-described electric toothbrushes have the following advantages:

- High degree of operational reliability due to a liquid-tight partition in the housing that separates the electrical components from the delivery system and reservoirs.
- Compact, convenient handle part.
- Reservoirs are easily replaced.
- Pumps are easily replaced.
- Delivery system protected from drying out by valves at the coupling sites.
- Improved oral hygiene through delivery of different care products from separate reservoirs into the bristle head.
- Optimal application of the active ingredients of the care products due to delivery with suitable volume flow profiles, i.e. different rates of delivery of the substances during tooth brushing.

LIST OF REFERENCE NUMERALS

1.1 First electric toothbrush
1.2 Second electric toothbrush
1.3 Third electric toothbrush
2. Handle part
3. Attachment part
4. Bristle head
5. Front end
6.1 First drive unit
6.2 Second drive unit
7.1 First electric motor
7.2 Second electric motor
8.1 First reservoir
8.2 Second reservoir
9.1 First liquid dental care product
9.2 Second liquid dental care product
10.1 First pump
10.2 Second pump
10.3 First diaphragm valve pump
10.4 Second diaphragm valve pump
11.1 First canal
11.2 Second canal
12. Disposable/rechargeable battery
13. First row
14. Second row
15.1 First lever
15.2 Second lever
16. Housing
17. Partition
18. Soft-elastic membrane
19. First chamber
20. Second chamber
21. Slide passage
21.1 First slide
21.2 Second slide
22. Cover part
23. Plastic foil
24. Twin container
25. Coupling part
25.1 Fixing device
26.1 First inlet valve
26.2 Second inlet valve
27.1 First outlet opening
27.2 Second outlet opening
28. Assembly
29. Gear box
30. Device
32.1 First drive pin
32.2 Second drive pin
33.1 First rotary joint
33.2 Second rotary joint
34.1 First tappet
34.2 Second tappet
35. Front housing wall
36. Electronic circuit board
37.1 First switch
37.2 Second switch
38.1 First soft-elastic housing wall zone
38.2 Second soft-elastic housing wall zone
39.1 First opening
39.2 Second opening
40.1 First neck
40.2 Second neck
41.1 First inlet
41.2 Second inlet
42.1 First outlet
42.2 Second outlet
43.1 First valve tappet
43.2 Second valve tappet
44.1 First sealing ring
44.2 Second sealing ring
45. Line
46.1 First connection
46.2 Second connection
46.3 Third connection
46.4 Fourth connection
A-B First back and forth movements
A'-B' First pumping movements
C-D Second back and forth movements
C'-D' Second pumping movements

What is claimed is:

1. An electric toothbrush having a handle part and an attachment part, wherein the handle part has a housing, in which first and second reservoirs for care substances, first and second pumps for delivering the care substances and first and second drive units for driving the first and second pumps are arranged, wherein the housing of the handle part is divided into a liquid-tight first chamber and a second chamber by a partition extending in the longitudinal direction of the housing, wherein the first and second drive units are arranged in the first chamber and the first and second reservoirs and the first and second pumps are arranged in the second chamber.

2. The electric toothbrush according to claim 1, wherein the partition has a liquid-tight slide passage and the transmission of a driving movement (A'-B') from the drive unit to the first pump takes place by means of the slide passage.

3. The electric toothbrush according to claim 1, wherein the partition is partially designed as soft-elastic, and the transmission of a driving movement (A'-B') from the drive unit to the first pump takes place in the soft-elastic region of the partition.

4. The electric toothbrush according to claim 2, wherein the transmission of the driving movement (A'-B') from the drive unit to the first pump takes place via a lever.

5. The electric toothbrush according to claim 1, wherein the attachment part is connected via a canal to the first pump and the first reservoir.

6. The electric toothbrush according to claim 1, wherein the attachment part is drivable by a drive unit that is arranged in the liquid-tight first chamber.

7. The electric toothbrush according to claim 6, wherein the drive unit for the attachment part and the drive unit for the pump are arranged in the first chamber, one behind the other in the longitudinal direction of the housing.

8. The electric toothbrush according to claim 1, wherein the first and second reservoirs are designed with a low-profile shape.

9. The electric toothbrush according to claim 1, wherein the first and second pumps are diaphragm valve pumps.

10. The electric toothbrush according to claim 1, wherein the first and/or second reservoir consists essentially of a plastic foil.

11. The electric toothbrush according to claim 10, wherein the first and the second reservoir are arranged side by side.

12. The electric toothbrush according claim 1, wherein the pumps are connected to a coupling part for connecting the reservoirs.

13. The electric toothbrush according to claim 12, wherein the coupling part has an inlet valve that is activated by connecting the reservoirs.

14. The electric toothbrush according to claim 1, wherein the first pump in combination with a first inlet and with a first outlet that is connected via a first canal forms an assembly or that the first and second pump in combination with a first and second inlet and with a first and a second outlet that are connected via a respective first and second canal form an assembly.

15. The electric toothbrush according to claim 1, wherein the two reservoirs are filled with different care products.

16. The electric toothbrush according to claim 1, wherein the second chamber has on its outside a recloseable cover part.

* * * * *